United States Patent
Chaves

(10) Patent No.: US 10,881,142 B2
(45) Date of Patent: Jan. 5, 2021

(54) ELECTRONIC SMOKING DEVICE AND ADDITIVE RESERVOIR FOR ELECTRONIC SMOKING DEVICE

(71) Applicant: Fontem Holdings 1 B.V., Amsterdam (NL)

(72) Inventor: Liliana Chaves, Hamburg (DE)

(73) Assignee: Fontem Holdings 1 B.V., Amsterdam (NL)

( * ) Notice: Subject to any disclaimer, the term of this patent is extended or adjusted under 35 U.S.C. 154(b) by 21 days.

(21) Appl. No.: 15/756,529

(22) PCT Filed: Aug. 19, 2016

(86) PCT No.: PCT/EP2016/069691
§ 371 (c)(1),
(2) Date: Feb. 28, 2018

(87) PCT Pub. No.: WO2017/036818
PCT Pub. Date: Mar. 9, 2017

(65) Prior Publication Data
US 2018/0242641 A1 Aug. 30, 2018

(30) Foreign Application Priority Data
Aug. 28, 2015 (EP) .................................. 15183020

(51) Int. Cl.
*A24F 47/00* (2020.01)
*A61M 11/04* (2006.01)
*A61M 16/00* (2006.01)

(52) U.S. Cl.
CPC .......... *A24F 47/008* (2013.01); *A61M 11/042* (2014.02); *A61M 2016/0024* (2013.01)

(58) Field of Classification Search
CPC ....................................................... A24F 47/008
USPC ........................................................... 131/329
See application file for complete search history.

(56) References Cited

U.S. PATENT DOCUMENTS

| | | | |
|---|---|---|---|
| 2014/0166029 A1 | 6/2014 | Weigensberg et al. | |
| 2015/0122277 A1* | 5/2015 | Frobisher | A24D 3/043 131/329 |
| 2016/0007654 A1* | 1/2016 | Zhu | A24F 47/008 131/328 |
| 2016/0095356 A1* | 4/2016 | Chan | A24F 47/008 131/329 |
| 2016/0157522 A1* | 6/2016 | Zhu | A24F 47/008 131/329 |

(Continued)

FOREIGN PATENT DOCUMENTS

| CN | 2513025 Y | 9/2002 |
|---|---|---|
| CN | 2539534 Y | 3/2003 |

(Continued)

*Primary Examiner* — Eric Yaary
(74) *Attorney, Agent, or Firm* — Dykema Gossett PLLC

(57) ABSTRACT

The invention relates to electronic smoking devices (10) and to additive reservoirs (56) for electronic smoking devices (10). In order to be able to provide an additive that does not pass an atomizer (26) of the electronic smoking device (10), the invention provides that the electronic smoking devices (10) comprise an additive supply assembly (40) with at least one additive inlet opening (44) arranged at a distance to the atomizer (26), and that the additive reservoirs (56) comprises at least one additive outlet opening (66) in its inner lateral surface (60).

15 Claims, 3 Drawing Sheets

(56) References Cited

U.S. PATENT DOCUMENTS

| | | | |
|---|---|---|---|
| 2016/0219934 A1* | 8/2016 | Li | B65D 85/70 |
| 2016/0227838 A1* | 8/2016 | Johnson | A61M 15/06 |
| 2016/0302487 A1* | 10/2016 | Chen | F16K 3/0254 |
| 2017/0202265 A1* | 7/2017 | Hawes | A24F 40/40 |
| 2018/0014577 A1* | 1/2018 | Qiu | G06F 3/011 |
| 2018/0035718 A1* | 2/2018 | Liu | A24F 47/00 |

FOREIGN PATENT DOCUMENTS

| | | | |
|---|---|---|---|
| CN | 1708241 A | | 12/2005 |
| CN | 103025181 A | | 4/2013 |
| CN | 203137031 U | | 8/2013 |
| CN | 103974635 A | | 8/2014 |
| CN | 104248043 A | | 12/2014 |
| CN | 204146331 U | | 2/2015 |
| CN | 104432542 A | | 3/2015 |
| CN | 104544575 A | | 4/2015 |
| CN | 204466908 U | | 7/2015 |
| GB | 2513639 A | | 5/2014 |
| GB | 2515562 A | | 12/2014 |
| JP | 10198470 A | | 4/1989 |
| WO | 2014116974 A1 | | 7/2014 |
| WO | 2014132045 A3 | | 9/2014 |
| WO | 2015/000974 A1 | | 1/2015 |

* cited by examiner

ELECTRONIC SMOKING DEVICE AND ADDITIVE RESERVOIR FOR ELECTRONIC SMOKING DEVICE

FIELD OF INVENTION

The present invention relates generally to electronic smoking devices, in particular electronic cigarettes, and to additive reservoirs for electronic smoking devices.

BACKGROUND OF THE INVENTION

An electronic smoking device, such as an electronic cigarette (e-cigarette), typically has a housing accommodating an electric power source (e.g. a single use or rechargeable battery, electrical plug, or other power source), and an electrically operable atomizer. The atomizer vaporizes or atomizes liquid supplied from a reservoir and provides vaporized or atomized liquid as an aerosol. Control electronics control the activation of the atomizer. In some electronic cigarettes, an airflow sensor is provided within the electronic smoking device, which detects a user puffing on the device (e.g., by sensing an under-pressure or an air flow pattern through the device). The airflow sensor indicates or signals the puff to the control electronics to power up the device and generate vapor. In other e-cigarettes, a switch is used to power up the e-cigarette to generate a puff of vapor.

It is known to provide based liquids to be atomized with an electronic smoking device with a flavor.

SUMMARY OF THE INVENTION

In accordance with one aspect of the present invention, there is provided an electronic smoking device comprising an atomizer, an air inhalation port, and an additive supply assembly. The additive supply assembly comprises a duct interconnecting the atomizer and the air inhalation port and forming a flow path for the atomized liquid. The additive supply assembly comprises at least one additive inlet opening that opens the duct essentially perpendicularly to the flow path and is arranged at a distance to the atomizer. The electronic smoking device further comprising an additive reservoir comprising an additive storage volume and an inner lateral surface that at least section-wise extends around a central axis of the additive reservoir. The additive reservoir comprises at least one additive outlet opening in the inner lateral surface that opens the additive storage volume towards the central axis and that is configured to communicate with the additive inlet opening. In accordance with the other aspect of the present invention, there is provided an additive reservoir for an electronic smoking device, comprising an additive storage volume and an inner lateral surface that at least section-wise extends around a central axis of the additive reservoir, wherein the additive reservoir comprises at least one additive outlet opening in the inner lateral surface that opens the additive storage volume towards the central axis. The additive reservoir of the one aspect may be the additive reservoir of the other aspect.

The characteristics, features and advantages of this invention and the manner in which they are obtained as described above, will become more apparent and be more clearly understood in connection with the following description of exemplary embodiments, which are explained with reference to the accompanying drawings.

BRIEF DESCRIPTION OF THE DRAWINGS

In the drawings, same element numbers indicate same elements in each of the views.

DESCRIPTION OF THE PREFERRED EMBODIMENTS

Figure 1:
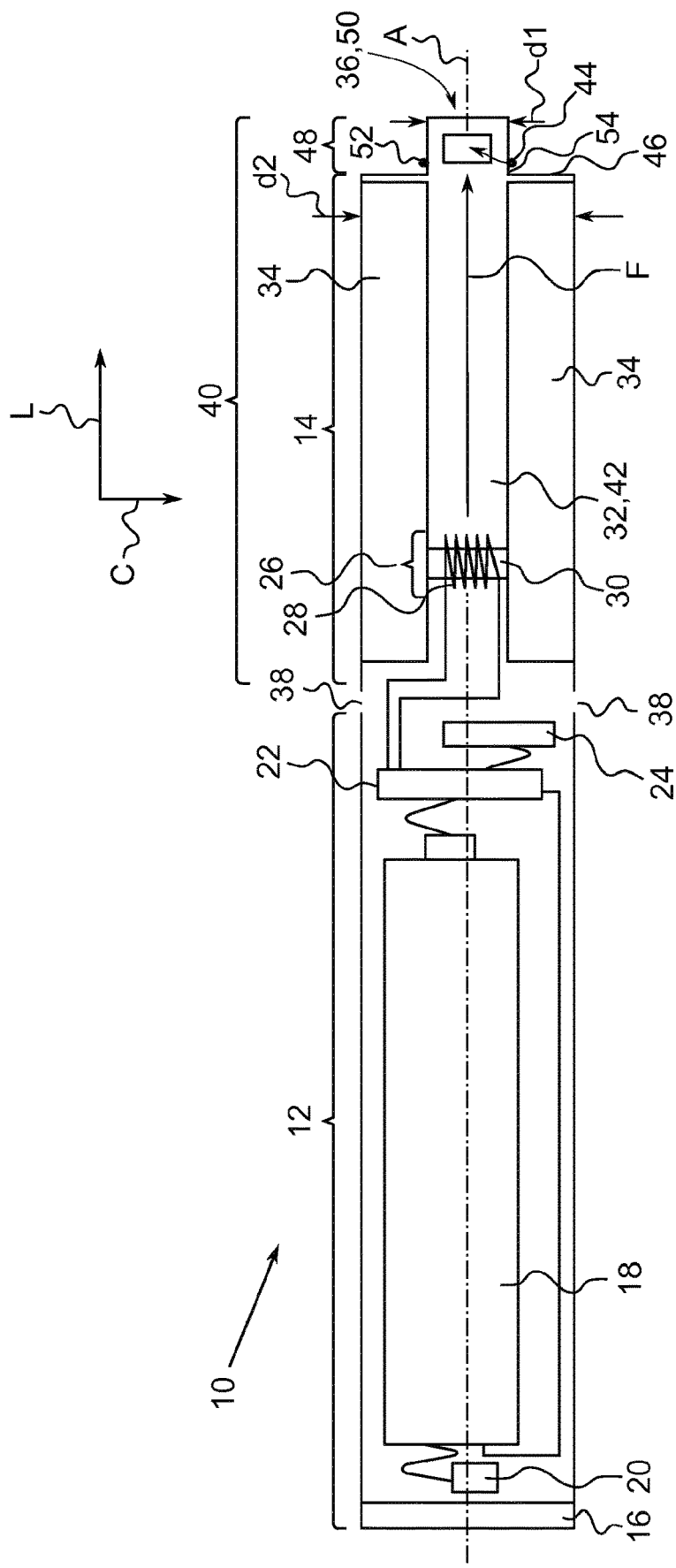
FIG. 1 is a schematic cross-sectional illustration of an exemplary electronic smoking device with an additive supply assembly.

Throughout the following, an electronic smoking device, for example an e-cigarette, will be described exemplarily. As is shown in FIG. 1, an electronic smoking device 10 typically has a housing comprising a cylindrical hollow tube having an end cap 16. The cylindrical hollow tube may be a single-piece or a multiple-piece tube. In FIG. 1, the cylindrical hollow tube is shown as a two-piece structure having a battery portion 12 and an atomizer/liquid reservoir portion 14. Together the battery portion 12 and the atomizer/liquid reservoir portion 14 form a cylindrical tube which can be approximately the same size and shape as a conventional cigarette, typically about 100 mm with a 7.5 mm diameter, although lengths may range from 70 to 150 or 180 mm, and diameters from 5 to 20 mm.

The battery portion 12 and atomizer/liquid reservoir portion 14 are typically made of metal, e.g. steel or aluminum, or of hardwearing plastic and act together with the end cap 16 to provide a housing to contain the components of the electronic smoking device 10. The battery portion 12 and an atomizer/liquid reservoir portion 14 may be configured to fit together by a friction push fit, a snap fit, or a bayonet attachment, magnetic fit, or screw threads. The end cap 16 is provided at the front end of the battery portion 12. The end cap 16 may be made from translucent plastic or other translucent material to allow an LED 20 positioned near the end cap to emit light through the end cap. The end cap can be made of metal or other materials that do not allow light to pass.

An air inlet may be provided in the end cap, at the edge of the inlet next to the cylindrical hollow tube, anywhere along the length of the cylindrical hollow tube, or at the connection of the battery portion 12 and the atomizer/liquid reservoir portion 14. FIG. 1 shows a pair of air inlets 38 provided at the intersection between the battery portion 12 and the atomizer/liquid reservoir portion 14.

A battery 18, the light-emitting diode (LED) 20, control electronics 22 and optionally an airflow sensor 24 are provided within the cylindrical hollow tube battery portion 12. The battery 18 is electrically connected to the control electronics 22, which are electrically connected to the LED 20 and the airflow sensor 24. In this example the LED 20 is at the front end of the battery portion 12, adjacent to the end cap 16 and the control electronics 22 and airflow sensor 24 are provided in the central cavity at the other end of the battery 18 adjacent the atomizer/liquid reservoir portion 14.

The airflow sensor 24 acts as a puff detector, detecting a user puffing or sucking on the atomizer/liquid reservoir portion 14 of the electronic smoking device 10. The airflow sensor 24 can be any suitable sensor for detecting changes in airflow or air pressure, such as a microphone switch including a deformable membrane which is caused to move by variations in air pressure. Alternatively the sensor may be a Hall element or an electro-mechanical sensor.

The control electronics 22 are also connected to an atomizer 26. In the example shown, the atomizer 26 includes a heating coil 28 which is wrapped around a wick 30 extending across a central passage 32 of the atomizer/liquid reservoir portion 14. The coil 28 may be positioned anywhere in the atomizer 26 and may be transverse or parallel to the liquid reservoir 34. The wick 30 and heating coil 28 do not completely block the central passage 32. Rather an air gap is provided on either side of the heating coil 28 enabling air to flow past the heating coil 28 and the wick 30. The atomizer may alternatively use other forms of heating elements, such as ceramic heaters, or fiber or mesh material heaters. Nonresistance heating elements such as sonic, piezo and jet spray may also be used in the atomizer in place of the heating coil.

The central passage 32 is surrounded by a cylindrical liquid reservoir 34 with the ends of the wick 30 abutting or extending into the liquid reservoir 34. The wick 30 may be a porous material such as a bundle of fiberglass fibers, with liquid in the liquid reservoir 34 drawn by capillary action from the ends of the wick 30 towards the central portion of the wick 30 encircled by the heating coil 28.

The liquid reservoir 34 may alternatively include wadding soaked in liquid which encircles the central passage 32 with the ends of the wick 30 abutting the wadding. In other embodiments the liquid reservoir 34 may comprise a toroidal cavity arranged to be filled with liquid and with the ends of the wick 30 extending into the toroidal cavity.

An air inhalation port 36 is provided at the back end of the atomizer/liquid reservoir portion 14 remote from the end cap 16. The inhalation port 36 may be formed by the cylindrical hollow tube atomizer/liquid reservoir portion 14 or may be formed in an end cap.

In use, a user sucks on the electronic smoking device 10. This causes air to be drawn into the electronic smoking device 10 via one or more air inlets, such as air inlets 38, and to be drawn through the central passage 32 towards the air inhalation port 36. The change in air pressure which arises is detected by the airflow sensor 24, which generates an electrical signal that is passed to the control electronics 22. In response to the signal, the control electronics 22 activate the heating coil 28, which causes liquid present in the wick 30 to be vaporized creating an aerosol (which may comprise gaseous and liquid components) within the central passage 32. As the user continues to suck on the electronic smoking device 10, this aerosol is drawn through the central passage 32 and inhaled by the user. At the same time the control electronics 22 also activate the LED 20 causing the LED 20 to light up which is visible via the translucent end cap 16 mimicking the appearance of a glowing ember at the end of a conventional cigarette. As liquid present in the wick 30 is converted into an aerosol more liquid is drawn into the wick 30 from the liquid reservoir 34 by capillary action and thus is available to be converted into an aerosol through subsequent activation of the heating coil 28.

Some electronic smoking devices are intended to be disposable and the electric power in the battery 18 is intended to be sufficient to vaporize the liquid contained within the liquid reservoir 34, after which the electronic smoking device 10 is thrown away. In other embodiments the battery 18 is rechargeable or replaceable and the liquid reservoir 34 is refillable or replaceable. In the cases where the liquid reservoir 34 is a toroidal cavity, this may be achieved by refilling the liquid reservoir 34 via a refill port. In other embodiments the atomizer/liquid reservoir portion 14 of the electronic smoking device 10 is detachable from the battery portion 12 and another atomizer/liquid reservoir portion 14 can be fitted with another liquid reservoir 34 thereby replenishing the supply of liquid. In some cases, replacing the liquid reservoir 34 may involve replacement of the heating coil 28 and the wick 30 along with the replacement of the liquid reservoir 34. A replaceable unit comprising the atomizer 26 and the liquid reservoir 34 is called a cartomizer.

The replacement liquid reservoir 34 may be in the form of a cartridge having a central passage 32 through which a user inhales aerosol via an air inhalation port 36. In other embodiments, aerosol may flow around the exterior of the cartridge 32 to the air inhalation port 36.

Of course, in addition to the above description of the structure and function of a typical electronic smoking device 10, variations also exist. For example, the LED 20 may be omitted. The airflow sensor 24 may be placed adjacent the end cap 16 rather than in the middle of the electronic smoking device. The airflow sensor 24 may be replaced with a switch which enables a user to activate the electronic smoking device manually rather than in response to the detection of a change in air flow or air pressure.

Different types of atomizers may be used. Thus for example, the atomizer may have a heating coil in a cavity in the interior of a porous body soaked in liquid. In this design aerosol is generated by evaporating the liquid within the porous body either by activation of the coil heating the porous body or alternatively by the heated air passing over or through the porous body. Alternatively the atomizer may use a piezoelectric atomizer to create an aerosol either in combination or in the absence of a heater.

The central passage 32 forms a duct 42 that interconnects the atomizer 26 and the air inhalation port 36 in a gas-conductive manner, such that vaporized liquid is transported from the atomizer 26 to the air inhalation port 36 via the duct when the electronic smoking device 10 is used by a user. The duct 42 may extend along the liquid reservoir 34 instead of through the liquid reservoir 34.

The electronic smoking device 10 of the exemplary embodiment of FIG. 1 comprises an additive supply assembly 40, which is shown with the atomizer 26. Yet, the additive supply assembly 40 can be formed without the atomizer 26, such that the additive supply assembly 40 comprises the liquid reservoir 34 for liquid to be atomized by the electronic smoking device 10 and in particular by the atomizer 26. Hence, the atomizer 26 can be provided separately from the additive supply assembly 40. The additive supply assembly 40 comprises the duct 42 for conducting atomized liquid along a flow path F that extends through the duct 42 towards the air inhalation port 36 and begins, for example, at the atomizer 26.

The additive supply assembly 40 may comprise a liquid reservoir 34 for liquid to be atomized by the electronic smoking device 10. The additive supply assembly 40 may be provided without the atomizer 26. In case the additive supply assembly 40 comprises the atomizer 26, the additive supply assembly 40 may be designated as atomizer/liquid reservoir portion 14 or as cartomizer.

The additive supply assembly 40 for the electronic smoking device 10 may be provided as a replaceable module that is replaceable against another additive supply assembly 40.

The additive supply assembly 40 comprises at least one additive inlet opening 44 that opens the duct 42 essentially perpendicularly to the flow path F. Along the flow path F, the at least one additive inlet opening 44 is arranged downstream of the atomizer 26 and/or of the liquid reservoir 34.

Thus, the duct of the electronic smoking device 10 is the duct 42 of the additive supply assembly 40, which e.g. forms the central passage 32.

In the cross-sectional view of FIG. 1, the additive supply assembly 40 is shown with one additive inlet opening 44, only. Yet, the additive supply assembly 40 can comprise more than one inlet opening 44. For example, the additive inlet openings 44 are arranged at a distance to each other in a circumferential direction C of the duct 42. The circumferential direction C extends perpendicular to a longitudinal direction L, wherein the longitudinal direction L extends parallel to a central axis A of the duct. For example, the additive inlet openings 44 are arranged on a level with each other or within the same plane in the longitudinal direction L. The circumferential direction C is the circumferential direction C of the electronic smoking device 10, the longitudinal direction L is the longitudinal direction L of the electronic smoking device 10 and the central axis A is the central axis A of the electronic smoking device 10 according to the exemplary embodiment of FIG. 1.

In case more than one additive inlet opening 44 is provided, at least some or all of the additive inlet openings 44 can be arranged rotationally symmetric around the central axis A. In case the additive supply assembly 40 comprises exactly two additive inlet openings 44, the two additive inlet openings 44 are arranged opposite of each other.

The duct 42 at least section-wise protrudes from a main body 46 of the additive supply assembly 40. For example, the main body 46 forms at least a part of the housing of the atomizer/liquid reservoir portion 14 or of the electronic smoking device 10 and for example at least sectionwise the hollow tube. The liquid reservoir 34 may be arranged completely within the main body 46.

The duct 42 protrudes at least section-wise from the main body 46 in the longitudinal direction L. The duct 42 comprises an outer diameter $d_1$ that is smaller than an outer diameter $d_2$ of the main body 46 adjacent to a protruding section 48 of the duct 42. For example, it is the protruding section 48 that comprises the at least one additive inlet opening 44.

In order to provide that the user can consume vaporized liquid via the duct 42, the duct 42 opens into or even forms the air inhalation port 36 at a longitudinal end 50, e.g. the back end, of the duct 42 that points into the longitudinal direction L.

The additive supply assembly 40 comprises a fixing element 52 for affixing an additive reservoir. The fixing element 52 is shown as a latch element that protrudes from the protruding section 48 and away from the central axis A. Alternatively, the latch element may form a recess or a groove that opens away from the central axis A. For example, the fixing element 52 extends at least section-wise or even completely around the central axis A and is placed on a lateral surface 54 of the duct 42.

Alternatively, at least two or even more fixing elements 52 can be provided, for example on the lateral surface 54. The fixing elements 52 may be arranged one after the other along the circumferential direction C and may be distributed around the central axis A in a rotationally symmetric manner.

Figure 2:
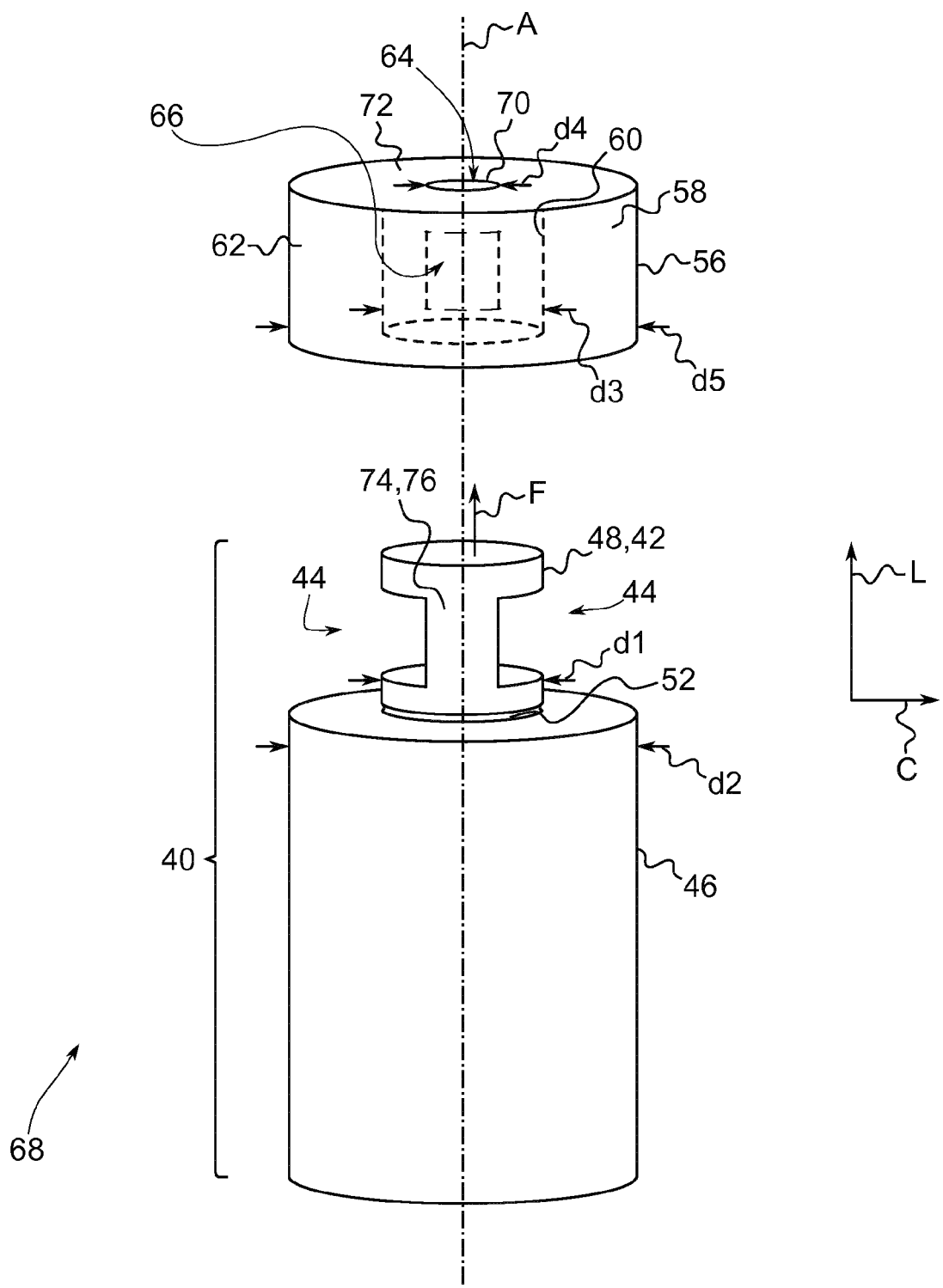
FIG. 2 schematically shows the exemplary embodiment of the electronic smoking device of FIG. 1 with an additive reservoir in a perspective view.

FIG. 2 shows the additive supply assembly 40 of FIG. 1 with an exemplary embodiment of an additive reservoir in a schematic perspective view. For the sake of brevity, only the differences from the exemplary embodiment of FIG. 1 are looked at.

The additive supply assembly 40 is shown in FIG. 2 without the atomizer/liquid reservoir portion 14 and comprises the liquid reservoir 34 and optionally the atomizer 26, such that the additive supply assembly 40 can be designated as replacement liquid reservoir. In case the additive supply assembly 40 additionally comprises the atomizer 26, the additive supply assembly 40 may be designated as atomizer/liquid reservoir portion 14, e.g. as cartomizer or clearomizer.

The duct 42 is shown with two additive inlet openings 44. The two additive inlet openings 44 are arranged opposite of each other with respect to the central axis A. Independent of the amount of the additive inlet openings 44, a total dimension of the additive inlet openings 44 along the circumferential direction C is equal or smaller than a total dimension of sections of the duct 42 arranged between the additive inlet openings 44 in the circumferential direction C.

FIG. 2 shows the additive supply assembly 40 with an additive reservoir 56 for the electronic smoking device 10. The additive reservoir 56 comprises an additive storage volume 58 that is arranged between an inner lateral surface 60 and an outer lateral surface 62 of the additive reservoir 56. The inner lateral surface 60 at least section-wise extends around a central axis of the additive reservoir 56, e.g. for more than 180°. For example, the additive reservoir 56 completely extends around the central axis, e.g. for more than 180°. The additive reservoir 56 is e.g. C-shaped and opens perpendicular to the central axis, such that it can be clicked on the protruding section 48 of the duct 42. Hence, such an additive reservoir 56 can be designated as additive click-on. In FIG. 2, however, the fixing element 52 and in particular its inner lateral surface 60 completely surrounds the central axis, such that the additive reservoir 56 can be placed onto the protruding section 48 of the duct 42 and can be designated as an additive sleeve. The inner lateral surface 60 extends along the central axis. In FIG. 2, the central axis of the additive reservoir 56 is aligned with the central axis A, such that the central axis of the additive reservoir 56 is not shown separately.

Hence, through the additive reservoir 56, a through hole 64 extends along the central axis, such that at least the protruding section 48 of the duct 42 can be at least partly be inserted into the additive reservoir 56 and into its through hole 64, along the central axis A, such that the flow path F extends through the additive reservoir 56 and in particular through the through hole 64. The air inhalation port 36 opens into the through hole 64 in case the additive reservoir 56 is added to the additive supply assembly 40, such that a user of the additive supply assembly 40 with the additive reservoir 56 can consume vaporized liquid from the electronic smoking device 10 that is equipped with the additive supply assembly 40 and the additive reservoir 56.

The additive reservoir 56 comprises at least one additive outlet opening 66 in the inner lateral surface 60. The additive outlet opening 66 opens the additive storage volume 58 towards the central axis and for example into the through hole 64.

In particular, in case the additive supply assembly 40 comprises more than one additive inlet opening 44, the additive reservoir 56 comprises more than one additive outlet opening 66. The additive outlet openings 66 are arranged at a distance to each other in a circumferential direction of the additive reservoir 56. The circumferential direction of the additive reservoir 56 corresponds to the circumferential direction C of the duct 42, such that the circumferential direction of the additive reservoir 56 is not shown separately.

The amount, size and/or arrangement of the additive inlet opening 44 or the additive inlet openings 44 can correspond to the amount, size and/or arrangement of the additive outlet openings 66 in case the additive reservoir 56 is placed onto the duct 42 against the longitudinal direction L.

Hence, at least some or al of the additive outlet openings 66 can be arranged rotationally symmetric around the central axis. In case the additive reservoir 56 comprises exactly two additive outlet openings 66, the two additive inlet openings 66 are for example arranged opposite of each other with respect to the central axis.

A total dimension of sections of the inner lateral surface 60 around the central axis and for example between the additive outlet opening 66 or the additive outlet openings 66 in the circumferential direction can be equal to or greater than a total dimension of the at least one additive outlet opening 66 around the central axis. In case the additive reservoir 56 comprises more than one additive outlet opening 66, the total dimension of all of the additive outlet openings 66 is smaller than the total dimension of all sections of the inner lateral surface 60 that are arranged between or after the additive outlet openings 66 in the circumferential direction.

The additive supply assembly 40 and the additive reservoir 56 can be provided separately from each other. Alternatively, the additive supply assembly 40 and the additive reservoir 56 can form a kit 68, for example a retrofit kit for the electronic smoking device 10. The kit 68 can be used to replace liquid to be atomized and an additive by using the components of the kit 68, the components being the additive supply assembly 40 and the additive reservoir 56.

A maximum distance of different sections of the inner lateral surface 60 essentially corresponds to the outer diameter $d_1$ of the duct 42. For example, an inner diameter $d_3$ of the additive reservoir 56 and in particular of its through hole 64 essentially corresponds to the outer diameter $d_1$ of the duct 42 and in particular of its protruding section 48.

An opening 70 on a front face 72 of the additive reservoir 56 may have a diameter $d_4$ that is equal to or smaller than the inner diameter $d_3$. The front face 72 faces away from the additive supply assembly 40 in a state, in which the additive reservoir 56 is mounted to the additive supply assembly 40.

The fixing element 52 is exemplarily shown as a latch groove that extends around the central axis A in the circumferential direction C.

At least the protruding section 48 of the duct 42 can be pipe-shaped with a circular cross-section, such that the duct 42 forms a rotational bearing for the additive reservoir 56. Hence, the additive reservoir 56 can be rotated around the central axis A even if the additive reservoir 56 is mounted to the additive supply assembly 40. The additive reservoir 56 is mounted movably on the duct 42 such that a degree of overlap of the least one additive inlet opening 44 and the one additive outlet opening 66 is changeable Hence, when rotating the additive reservoir 56 in or against the circumferential direction C, the at least one additive outlet opening 66 can be brought in overlap with the at least one additive inlet opening 44, such that additive can exit the additive reservoir 56 via the at least one additive outlet opening 66 and can enter the flow path F via the at least one additive inlet opening 44. Due to the rotational arrangement of the additive reservoir 56, an overlapping area of the at least one additive outlet opening 66 and the at least one additive inlet opening 44 can be varied, such that the amount of additive entering the flow path F in a predetermined time period can be changed.

A maximum outer diameter $d_5$ of the additive reservoir 56 may correspond to the outer diameter $d_2$ of the additive supply assembly 40, e.g. of its main body 46, for example at least adjacent to the protruding section 48 of the duct 42.

Hence, when mounted to the additive supply assembly 40, the additive reservoir 56 does not protrude from the additive supply assembly 40 perpendicularly to the central axis A, but is flush with the additive supply assembly 40 perpendicularly to the central axis A.

A total dimension of a closed section 74 or of closed sections of an outer lateral surface 76 at least of the protruding section 48 of the duct 42 along the circumferential direction C of the duct 42 is equal to or greater than the total dimension of the at least one additive outlet opening 66 in the circumferential direction C. Hence, it is possible to rotate the additive reservoir 56 into a storage position, in which a minimum amount of or even no additive leaves the additive reservoir 56 and enters the flow path F.

Figure 3:
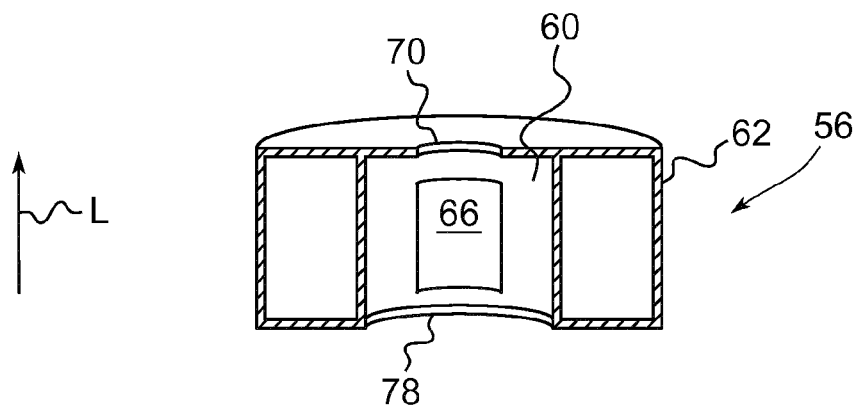
FIG. 3 shows schematically the exemplary embodiment of the additive reservoir of FIG. 2 in a cross-sectional view.

FIG. 3 shows the additive reservoir 56 of the exemplary embodiment of FIG. 2 in a cross-sectional view, wherein the cross-section extends along the central axis, which is, however, not shown for the sake of simplicity.

The additive reservoir 56 comprises a counter fixing element 78 for the fixing element 52 of the additive supply assembly 40. The counter fixing element 78 is exemplarily shown on the inner lateral surface 60 and at a longitudinal end of the additive reservoir 56 that faces against the longitudinal direction L. Such an arrangement of the counter fixing element 78 provides that the additive outlet opening 66 can have a maximum size along the longitudinal direction L.

The counter fixing element 78 preferably extends around the central axis of the additive reservoir 56 completely, such that the additive reservoir 56 remains to be fixed to the additive supply assembly 40 independently of its rotational position. The counter fixing element 78 is at least sectionwise formed complementary to the fixing element 52 and may be a latch protrusion or a latch recess. The latch protrusion protrudes from the inner lateral surface 60 towards the central axis. The latch recess extends away from the central axis and for example towards the outer lateral surface 62 into the inner lateral surface 60, but opens towards the central axis. Alternatively to the form fit of the latch elements, the additive reservoir 56 can be held on the duct 42 by a force fit, e.g. a friction fit, the force fit preventing that the additive reservoir 56 falls off of the duct 42, but allows for the rotational movement on the rotational bearing provided by the duct 42.

Figure 4:
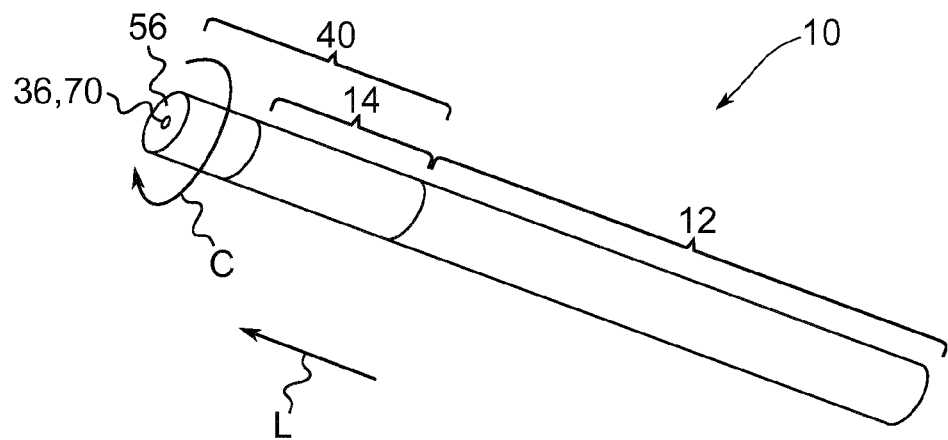
FIG. 4 shows the exemplary embodiment of the electronic smoking device of FIGS. 1 and 2 with the additive reservoir mounted.

FIG. 4 shows the electronic smoking device 10 with the additive supply assembly 40 and the additive reservoir 56 in a mounted state, in which the electronic smoking device 10 is ready for use. The additive supply assembly 40 can comprise the atomizer/liquid reservoir portion 14, which is shown attached to the battery portion 12. The additive reservoir 56 is rotatable in the circumferential direction C with respect to the additive supply assembly 40 and for example with respect to the duct 42 in order to adapt the amount of additive to be added to atomized liquid that travels along the flow path F towards the air inhalation port 36, which may be provided by the opening 70.

The additive reservoir 56 comprises an additive that may comprise compounds with a volatility higher than water and for example higher than the liquid to be atomized. For example, the compounds of the additive may have an evaporation number less than 10, less than 8, less than 5, less than 2.5, and for example of 8.3. Alternatively, the compounds of the additive may have an evaporation rate greater than 3, greater than 5 or greater than 8, for example an evaporation rate of 3.8.

Furthermore, the additive may comprise a flavored material and/or nicotine, wherein the flavored material and/or the nicotine exits the second storage volume 42 at room temperature and under ambient pressure by evaporation without heating or other action of the atomizer 26 or of another atomizer.

The flavored materials are for example esters, such as isoamyl acetate, linalyl acetate, isoamyl propionate, linalyl butyrate and the like or natural essential oils as plant essential oils, such as spearmint, peppermint, *cassia*, jasmine and the like or animal essential oils, such as musk, amber, civet, castor and the like or simple flavoring materials, such as anethole, limonene, linalool, eugenol and the like or hydrophilic flavor components such as a leaf tobacco extract or natural plant flavoring materials such as licorice, St. John's wort, a plum extract, a peach extract and the like or acids such as a malic acid, tartaric acid, citric acid and the like or sugars such as glucose, fructose, isomerized sugar and the like or polyhydric alcohols such as propylene glycol, glycerol, sorbitol and the like. It is also possible to combine different flavored materials as mentioned above into new flavored materials. Moreover, it is possible to adsorb any flavor onto a solid material and to use this material as flavored material within an electronic smoking device according to the present invention.

Volatility is the tendency of a compound to become volatile/vaporized and it is directly related to the vapor pressure of said compound. At a given temperature and pressure, the volatility and, hence, vapor pressure of a compound is constant. The volatility of at least one and in particular of the flavor and/or of an aroma of the compounds of the additive may be provided with respect to the one of water, which may have a volatility of "1" and may be called evaporation number. A compound with a higher evaporation number than water has a higher vapor pressure than water—for example, at least one and in particular of the flavor and/or of the aroma compound of the compounds of the additive may have evaporation numbers between 3.8 and 10. In general, aroma compounds are highly volatile and this is the reason why we can smell them at room temperature. In case the flavor and/or the aroma compound has a volatility that is insufficient for the compound to be vaporized during use of the electronic smoking device, the flavor and/or of the aroma compound may be combined and for example mixed with another material with a sufficient volatility that entrains the flavor and/or of the aroma compound when the other material vaporizes.

The evaporation number may be defined as the ratio of time spent to completely evaporate a certain amount of solvent at 20° C. temperature and 65% relative humidity, to the time spent to completely evaporate the same amount of a reference solvent under same conditions. For example, diethyl ether or n-butyl acetate may be used as the reference solvent.

In summary, according to an aspect, the electronic smoking device comprises an atomizer, an air inhalation port, and an additive supply assembly that comprises a duct interconnecting the atomizer and the air inhalation port and forming a flow path. The additive supply assembly comprises at least one additive inlet opening that opens the duct essentially perpendicularly to the flow path. The at least one additive inlet opening is arranged at a distance to the atomizer. The electronic smoking device further comprises an additive reservoir, the additive reservoir comprising an additive storage volume and an inner lateral surface that at least section-wise extends around a central axis of the additive reservoir, e.g. for more than 180°, wherein the additive reservoir comprises at least one additive outlet opening in the inner lateral surface that opens the additive storage volume towards the central axis and that is configured to communicate with the additive inlet opening. According to another aspect, an additive reservoir for the electronic smoking device according to the previous aspect is provided, the additive reservoir comprising an additive storage volume and an inner lateral surface that at least section-wise extends around a central axis of the additive reservoir, e.g. for more than 180°, wherein the additive reservoir comprises at least one additive outlet opening in the inner lateral surface that opens the additive storage volume towards the central axis.

An advantage of the above aspects may be that, due to the distance between the atomizer and the additive outlet opening, an additive and, for example, a flavor can be added to the electronic smoking device at the user's choice in order to be consumed by a user of the electronic smoking device, wherein the additive is not atomized by the atomizer.

The additive supply assembly may comprise a liquid reservoir for liquid to be atomized by the electronic smoking device. The additive supply assembly may be provided without the atomizer. In case the additive supply assembly comprises the atomizer, the additive supply assembly may be designated as atomizer/liquid reservoir portion or as cartomizer.

The additive supply assembly for the electronic smoking device may be provided as a replaceable module that is replaceable against another additive supply assembly, wherein the function and structure of the other additive supply assembly may correspond to the additive supply assembly of the electronic smoking device and may comprise a liquid reservoir for liquid to be atomized by an electronic smoking device. The additive reservoir for the electronic smoking device may be provided as a replaceable module that is replaceable against another additive reservoir, wherein the function and structure of the other additive reservoir may correspond to the additive reservoir of the electronic smoking device.

The additive reservoir may comprise a duct for conducting atomized liquid along a flow path, wherein the additive supply assembly comprises at least additive inlet opening that opens the duct essentially perpendicularly to the flow path.

The additive reservoir for the electronic smoking device may be provided separate from the electronic smoking device and for example alone or with at least one other additive reservoir, or with the additive supply assembly as a kit for the electronic smoking device. The function and structure of the replacement additive reservoir may correspond to the function and structure of the replacement additive reservoir of the electronic smoking device and may comprise an additive storage volume and an inner lateral surface that at least section-wise extends around a central axis of the additive reservoir, e.g. for more than 180°. The additive reservoir comprises at least one additive outlet opening in the inner lateral surface that opens the additive storage volume towards the central axis. In case the kit comprises the additive supply assembly and the additive reservoir a maximum distance of different sections of the inner lateral surface to each other may correspond to an outer diameter of the duct.

The additive supply assembly, the additive reservoir and/or the kit are advantageous independently of the electronic smoking device and may form replacement product that can be provided with or separate from the electronic smoking device. Hence, the electronic smoking device may be provided with or without the additive reservoir and/or with or without the additive supply assembly Thus, the additive supply assembly of or for the electronic smoking device may comprise the liquid reservoir for liquid to be atomized by an electronic smoking device. The additive supply assembly may comprise the duct for conducting atomized liquid along the flow path. Further, the additive supply assembly may comprise at least one additive inlet opening that opens the duct essentially perpendicularly to the flow path.

The additive reservoir of or for the electronic smoking device may comprise the additive storage volume and the inner lateral surface. The inner lateral surface may at least section-wise extend around a central axis of the additive reservoir, e.g. for more than 180°. Further, the additive reservoir may comprise the at least one additive outlet opening in the inner lateral surface. The additive outlet opening may open the additive storage volume towards the longitudinal axis.

The additive reservoir 56 may for example be C-shaped and open perpendicular to the central axis, such that it can be clicked on the protruding section of the duct. Hence, such an additive reservoir can be designated as additive click-on. However, the fixing element and in particular its inner lateral surface may completely surround the central axis, such that the additive reservoir can be placed onto the protruding section of the duct and can be designated as an additive sleeve.

The kit may comprise the additive supply assembly and the additive reservoir. The maximum distance of different sections of the inner lateral surface of the additive reservoir to each other may correspond to the outer diameter of the duct of the additive supply assembly.

The electronic smoking device may comprise the atomizer, the air inhalation port, and the duct interconnecting the atomizer and the air inhalation port. The electronic smoking device may further comprise the additive supply assembly. Alternatively, the electronic smoking device may comprise the kit. The duct of the electronic smoking device is the duct of the additive supply assembly.

Along the flow path, the at least one inlet opening may be arranged downstream of the atomizer and/or of the liquid reservoir. An advantage of this embodiment may be that the flavor mixed with atomized liquid does not accumulate at the atomizer, such that different flavors can be used without an undesired mixing of the flavors in the atomizer. Furthermore, the additive does not pass the atomizer and is, thus, not heated by the atomizer in case the atomizer vaporizes liquid, thereby avoided undesirable heat treatment of the additive.

The additive supply assembly may comprise more than one inlet opening, wherein the additive inlet openings are arranged at a distance to each other in a circumferential direction of the duct. An advantage of such an additive supply assembly may be that additive can be added to the flow path from different sites and/or in high quantities.

At least some or even all of the additive inlet openings can be arranged rotationally symmetric around a central axis of the duct. An advantage of such an additive supply assembly may be that additive can be uniformly distributed when it is added to the flow path.

The additive supply assembly may comprise exactly two additive inlet openings that are arranged opposite of each other. Hence, an advantage of such an additive supply assembly may be that the additive can be uniformly distributed without increasing effort for producing the additive supply assembly unnecessarily, which be formed by injecting molding.

The duct may at least section-wise protrude from a main body of the additive supply assembly and may comprise an outer diameter that is smaller than an outer diameter of a main body of the additive supply assembly adjacent to a protruding section of the duct. An advantage of such a duct may be that the additive reservoir can be easily mounted and for example be attached or positioned onto the duct.

It may be the protruding section that comprises the at least one additive inlet opening. An advantage of such a duct with a protruding section that comprises the at least one additive inlet opening may be that the at least one additive inlet opening is readily accessible for the additive reservoir.

The additive reservoir may comprise more than one additive outlet opening, wherein the additive outlet openings are arranged at a distance to each other in a circumferential direction of the additive reservoir. In particular, the amount, arrangement and/or size of the additive outlet openings may correspond to the amount, arrangement and/or size of the inlet openings, such that additive can readily flow from the additive reservoir into the duct and the flow path.

The additive outlet openings can be arranged rotationally symmetric around the central axis. An advantage of such an additive reservoir may be that the additive is injected into the flow path with a uniform distribution.

The additive reservoir may comprise exactly two additive outlet openings that are arranged opposite of each other, e.g. with respect to the central axis. Hence, an advantage of such an additive reservoir may be that the additive reservoir can be easily produced, e.g. by injection molding, without affecting the uniform distribution of the additive when it is added to the flow path.

A total dimension and for example a width of the inner lateral surface around the central axis may be equal to or greater than a total dimension and for example a width of the at least one additive outlet opening, or the additive outlet openings, around the central axis. An advantage of such an additive reservoir may be that at least one rotational position of the additive reservoir exists in which the additive reservoir is mounted to the additive supply assembly and in which a flow of additive from the additive reservoir into the duct and/or the flow path is blocked by the additive supply assembly.

The duct may form a rotational bearing for the additive reservoir. Hence, the additive reservoir may be mounted movably on the duct such that a degree of overlap of the least one additive inlet opening and the one additive outlet opening is changeable. An advantage of such an embodiment may be that it is possible to adjust the flow of additive from the additive reservoir into the additive supply assembly, and in particular into the flow path, by rotating the additive reservoir on the duct, thereby changing an overlap between the at least one additive inlet opening and the least one additive outlet opening.

A maximum outer diameter of the additive reservoir may correspond to an outer diameter of the main body, e.g. adjacent to the protruding section of the duct. An advantage of such an additive reservoir may be that the additive reservoir does not protrude from the additive supply assembly or from the electronic smoking device perpendicular to the central axis, thereby improving the operability of the additive supply assembly or of the electronic smoking device.

A total dimension of a closed section of an outer lateral surface of the duct along the circumferential direction of the duct can be equal to or greater than the total dimension of the at least one additive outlet opening. Hence, an advantage of such an embodiment may be that the flow of additive from the additive reservoir into the additive supply assembly can be blocked by the additive supply assembly and in particular by the closed section or closed sections of the outer lateral surface, in case the additive outlet openings completely overlap the closed sections.

The first storage volume may comprise a liquid to be atomized by an electronic smoking device, and the second storage volume may comprise a material, e.g. an additive, to be added to the atomized liquid. The liquid to be atomized may be a liquid that forms vapor. Optionally, the liquid to be atomized may comprise nicotine. The material stored in the second storage volume may comprise a flavored material to be mixed with the atomized liquid. Optionally, the nicotine may be present in the material in the second storage volume instead of in the liquid in the first storage volume. An advantage of such a liquid reservoir may be that materials that do not need to be atomized or vaporized can be mixed with the atomized liquid in order to be provided to the user. Atomizing materials may namely affect the materials. For example, the taste of a flavored material may change by atomization or vaporization, in particular due to thermal changes of the material.

The additive may comprise compounds with a volatility higher than water. The compounds may have an evaporation number of less than 10, less than 8, less than 5 or less than 2.5, for example an evaporation number of 8.3. The compounds may have an evaporation rate of more than 3, more than 5, or more than 8, for example an evaporation rate of 3.8.

Volatility is the tendency of a compound to become volatile/vaporized and it is directly related to the vapor pressure of said compound. At a given temperature and pressure, the volatility and, hence, vapor pressure of a compound is constant. The volatility of at least one and in particular of the flavor and/or of an aroma of the compounds of the additive may be provided with respect to the one of water, which may have a volatility of "1" and may be called evaporation number. A compound with a higher evaporation number than water has a higher vapor pressure than water— for example, at least one and in particular of the flavor and/or the aroma compound of the compounds of the additive may have evaporation numbers between 3.8 and 10. In general, aroma compounds are highly volatile and this is the reason why we can smell them at room temperature. In case the flavor and/or of the aroma compound has a volatility that is insufficient for the compound to be vaporized during use of the electronic smoking device, the flavor and/or of the aroma compound may be combined and for example mixed with another material with a sufficient volatility that entrains the flavor and/or of the aroma compound when the other material vaporizes.

The evaporation number may be defined as the ratio of time spent to completely evaporate a certain amount of solvent at 20° C. temperature and 65% relative humidity, to the time spent to completely evaporate the same amount of a reference solvent under same conditions. For example, diethyl ether or n-butyl acetate may be used as the reference solvent.

The flavored materials are for example esters, such as isoamyl acetate, linalyl acetate, isoamyl propionate, linalyl butyrate and the like or natural essential oils as plant essential oils, such as spearmint, peppermint, *cassia*, jasmine and the like or animal essential oils, such as musk, amber, civet, castor and the like or simple flavoring materials, such as anethole, limonene, linalool, eugenol and the like or hydrophilic flavor components such as a leaf tobacco extract or natural plant flavoring materials such as licorice, St. John's wort, a plum extract, a peach extract and the like or acids such as a malic acid, tartaric acid, citric acid and the like or sugars such as glucose, fructose, isomerized sugar and the like or polyhydric alcohols such as propylene glycol, glycerol, sorbitol and the like. It is also possible to combine different flavored materials as mentioned above into new flavored materials. Moreover, it is possible to adsorb any flavor onto a solid material and to apply this material as flavored material according to the present invention.

The additive reservoir may be provided separate from other components of the electronic smoking device and for example with at least one other additive reservoir, wherein the additive reservoir may have the same structure. Further, the electronic smoking device may be provided without the additive reservoir.

In case the additive reservoir is provided separate, the additive reservoir for an electronic smoking device may comprise the above mentioned features and for example the additive storage volume and the inner lateral surface that at least section-wise extends around the central axis of the additive reservoir, e.g. for more than 180°, wherein the additive reservoir comprises the at least one additive outlet opening in the inner lateral surface that opens the additive storage volume towards the central axis.

The additive reservoir may comprises more than one additive outlet opening, wherein the additive outlet openings are arranged at a distance to each other in a circumferential direction of the additive reservoir. At least some of the additive outlet openings are arranged rotationally symmetric around the central axis. For example, the additive reservoir may comprise exactly two additive outlet openings that are arranged opposite of each other.

While this invention has been described in connection with what is presently considered to be practical exemplary embodiments, it is to be understood that the invention is not limited to the disclosed embodiments, but, on the contrary, is intended to cover various modifications and equivalent arrangements included within the scope of the appended claims.

LIST OF REFERENCE SIGNS 10 electronic smoking device
12 battery portion
14 atomizer/liquid reservoir portion
16 end cap
18 battery
20 light-emitting diode (LED)
22 control electronics
24 airflow sensor
26 atomizer
28 heating coil
30 wick
32 central passage
34 liquid reservoir
36 air inhalation port
38 air inlets
40 additive supply assembly
42 duct
44 additive inlet opening
46 main body
48 protruding section
50 longitudinal end
52 fixing element
54 lateral surface
56 additive reservoir
58 additive storage volume 60 inner lateral surface
62 outer lateral surface
64 through hole
66 additive outlet opening
68 kit
70 opening
72 front face
74 closed section
76 outer lateral surface
78 counter fixing element
$d_1$ outer diameter of duct 42
$d_2$ outer diameter of main body 46
$d_3$ inner diameter of additive reservoir 56
$d_4$ diameter of opening 70
$d_5$ outer diameter of additive reservoir 56
A central axis
C circumferential direction
F flow path
L longitudinal direction

The invention claimed is:

1. Electronic smoking device comprising:
   an atomizer;
   an air inhalation port;
   an additive supply assembly including
      a duct interconnecting the atomizer and the air inhalation port and forming a flow path, and
      at least one additive inlet opening that opens the duct essentially perpendicularly to the flow path and is arranged at a distance to the atomizer; and
   an additive reservoir including
      an additive storage volume,
      an inner lateral surface that at least section-wise extends around a central axis of the additive reservoir, and
      at least one additive outlet opening in the inner lateral surface that opens the additive storage volume towards the central axis and that is configured to communicate with the additive inlet opening;
   wherein a portion of the duct is configured to act as a rotational bearing for the additive reservoir when the additive reservoir is rotated around the duct.

2. Electronic smoking device according to claim 1, wherein the duct including
   a protruding section that protrudes from a main body of the additive supply assembly, and
   a first outer diameter that is smaller than a second outer diameter of the main body adjacent to a protruding section of the duct.

3. Electronic smoking device according to claim 2, wherein the protruding section includes the at least one additive inlet opening.

4. Electronic smoking device according to claim 1, wherein the additive reservoir is mounted movably on the duct, such that a degree of overlap of the least one additive inlet opening and the one additive outlet opening is changeable.

5. Electronic smoking device according to claim 1, wherein the duct includes an outer lateral surface, and the outer lateral surface includes a closed section with a total dimension along a circumferential direction of the duct that is equal to or greater than the total dimension of the at least one additive outlet opening.

6. Electronic smoking device according to claim 1, wherein the additive supply assembly further includes more than one additive inlet opening, wherein the additive inlet openings are arranged at a distance to each other in a direction perpendicular to the central axis of the duct.

7. Electronic smoking device according to claim 1, wherein the additive reservoir includes more than one additive outlet opening, wherein the additive outlet openings are arranged at a distance to each other in a direction perpendicular to the central axis of the additive reservoir.

8. Electronic smoking device according to claim 6, wherein at least some of the additive inlet openings are arranged rotationally symmetric around a central axis of the duct.

9. Electronic smoking device according to claim 7, wherein at least some of the additive outlet openings are arranged rotationally symmetric along the circumferential direction.

10. Electronic smoking device according to claim 1, wherein the additive supply assembly includes exactly two additive inlet openings arranged opposite of each other.

11. Electronic smoking device according to claim 1, wherein the additive reservoir includes exactly two additive outlet openings arranged opposite of each other.

12. Electronic smoking device according to claim 1, wherein a maximum distance of different sections of the inner lateral surface to each other corresponds to an outer diameter of the duct.

13. Electronic smoking device according to claim 1, wherein a maximum outer diameter of the additive reservoir corresponds to an outer diameter of the additive supply assembly.

14. Electronic smoking device according to claim 7, wherein at least some of the additive inlet openings are arranged rotationally symmetric around a central axis of the duct.

15. Electronic smoking device according to claim 8, wherein at least some of the additive outlet openings are arranged rotationally symmetric along the circumferential direction.

* * * * *